United States Patent [19]

Etheridge

[11] 4,030,369

[45] June 21, 1977

[54] AUTOMATIC CONTROL SYSTEM FOR VACUUM LOOP SAMPLE INJECTION SYSTEM

[75] Inventor: Jay D. Etheridge, Sand Springs, Okla.

[73] Assignee: Sun Oil Company of Pennsylvania, Philadelphia, Pa.

[22] Filed: Sept. 30, 1976

[21] Appl. No.: 728,491

Related U.S. Application Data

[63] Continuation-in-part of Ser. No. 668,780, March 19, 1976.

[52] U.S. Cl. .......................................... 73/422 GC
[51] Int. Cl.² ......................................... G01N 1/22
[58] Field of Search ...................... 73/422 GC, 23, 1

[56] References Cited

UNITED STATES PATENTS

| | | | |
|---|---|---|---|
| 2,964,938 | 12/1960 | Fuller | 73/422 GC |
| 3,501,961 | 3/1970 | Hable | 73/422 GC |
| 3,915,013 | 10/1975 | Gaeke | 73/422 GC |

*Primary Examiner*—S. Clement Swisher
*Attorney, Agent, or Firm*—Donald R. Johnson; J. Edward Hess

[57] ABSTRACT

A vacuum loop sample injection system, for use with gas chromatographs and other similar analyzer devices, in which the sample volume is collected within an enclosure having a known pressure, temperature, and volume so that the molecular quantity of a sample is used for each chromatograph test. The sample injection system operates by creating a vacuum within this enclosure and using this vacuum to slowly draw the sample in through a restriction until the predetermined pressure is obtained. The enclosure can be evacuated again by the vacuum source and refilled with the sample as many times as desired to wash any impurities out of the enclosure. Then the enclosure is placed in stream with the carrier gas for injection of the sample into the sample analyzer.

An automatic system for controlling the injection system operation is provided wherein a given number of sample containers can be connected to the system and a sequential operation commenced to inject the sample into the sample analyzer. The system permits the number of rinses for each enclosure and the number of injections of each sample, after a series of rinsing cycles, to be preselected and automatically ceases operation when the sample from the last container has been injected the preset number of times.

13 Claims, 5 Drawing Figures

STEP 1 POSITION

STEP 2 POSITION

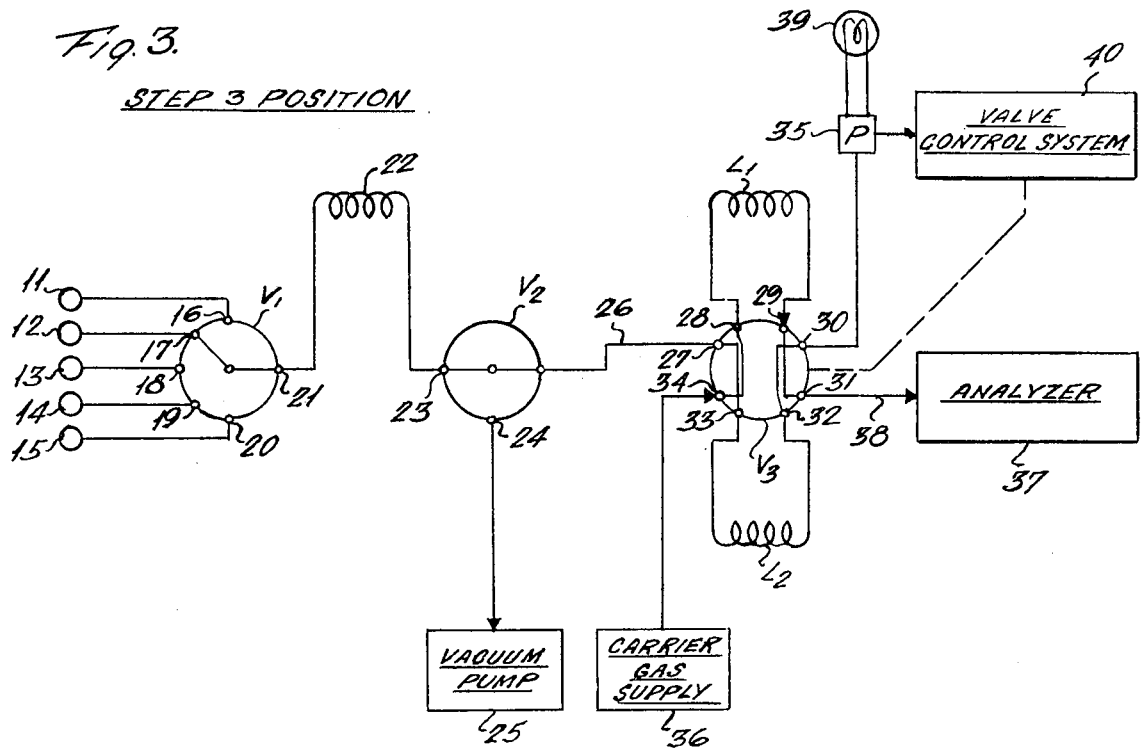
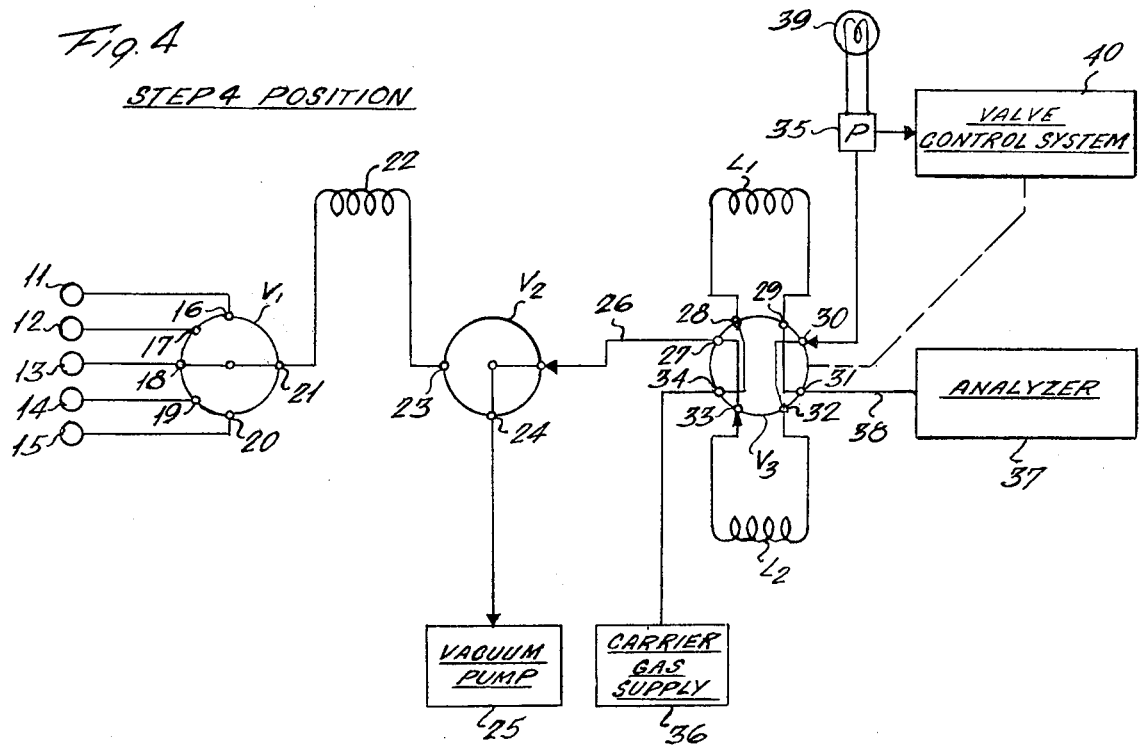

AUTOMATIC CONTROL SYSTEM FOR VACUUM LOOP SAMPLE INJECTION SYSTEM

REFERENCE TO RELATED APPLICATION

This application is a continuation-in-part of a copending patent application entitled "Sample Injection System for Analyzers", Ser. No. 668,780, filed Mar. 19, 1976 in which the additional subject matter relates to an automatic system for controlling the injection system operation.

BACKGROUND OF THE INVENTION

This invention is related to sample injection systems for gas chromatographs and other similar analyzer devices, and more specifically to a sample injection system using a source of vacuum to obtain the sample, as well as to a system for automatically controlling the sequential operation of the injection system.

There are several desirable requirements which should be met for a sample injection system. To achieve reliable, reproducible results, the sampling system should be able to inject a reproducible molecular quantity of sample each time. The injection system should also be designed to permit impurities to be washed out of the system before a sample is injected, so that the possibility of contamination of the sample from a previous sample is minimized. Preferably, the sampling system should be versatile enough so that it can receive samples contained at less than atmospheric pressure, as well as above. Another requirement for a sampling system is that it should be designed for efficient use of the sample by minimizing the amount of sample wasted and the amount of sample required for washing out the sampling system. In some instances, it is desirable that the sample injection system be designed so that it can be automated, so that continuous testing can be conducted as well as for obtaining better reproducability of results.

One of the problems today is that many of the sample injection systems available in the prior art fail to achieve all of the above noted requirements. One system in the prior art is a gas sampling valve in which the volume is trapped in a passage in the valve and quickly introduced into the carrier gas flow. In this system, temperature and volume can be accurately determined, but since the pressure is related to the flow rate, it often cannot be determined as accurately as is required. This system also fails to meet the requirements of sampling efficiency and the problems of being able to work with samples at less than atmospheric pressure.

Another method of obtaining a sample volume and injecting it in an analyzer is to use the gas type syringe. This sampling system has problems meeting the requirements for reproductability of the sample size, because of the small volumes needed for analyzers, as well as the desirability that the system be easily adaptable to sample automation.

SUMMARY OF THE INVENTION

In accordance with a preferred embodiment, a vacuum loop sample injection system for a chromatograph or other similar analyzer instrument is provided. Included in the sampling system is an enclosure having a known volume which is connected to a valve which can be switched in a sequence so that this enclosure is first evacuated by a vacuum pump, then connected to a source of sample fluid so that the pressure difference between the enclosure and the source container causes the sample to slowly flow through a restrictor and into the enclosure, and finally connected to a carrier gas supply when the pressure within the enclosure has reached a predetermined amount, wherein the sample trapped within the enclosure is carried by the carrier gas into the gas chromatograph system or other analyzer. For purposes of rinsing the enclosure to clean out contaminants, instead of immediately connecting the enclosure to the carrier gas, it can again be connected to the vacuum pump and then to the same sample source as many times as is deemed necessary before connection to the carrier gas for injection into the analyzer instrument. A pressure sensor system connected to the enclosure indicates when the predetermined pressure has been reached. Included also in this sample injection system is a system for selecting the sample source which is to be connected to the enclosure for injection into the chromatograph.

Also provided is an alternative embodiment wherein the sample injection system is automatically operated by a control system. The control system is designed to rinse out a sample enclosure a predetermined number of times and then inject the sample in the enclosure into the sample analyzer. This sequence is repeated a predetermined number of times so that several readings from the analyzer system for the same sample can be compared. Then the next sample is connected to the injection system to be placed through the same sequential operation. This continues until the last sample has been injected into the sample analyzer the predetermined number of times.

This sample injection system meets all of the above requirements noted for a gas sampling system for a chromatograph. Since the entire system can be mounted in an oven and maintained at a constant temperature, the volume of the enclosure is constant, and the same pressure is obtained each time a sample is isolated within the enclosure, and the same molecular quantity of sample will be injected into the gas chromatograph or other analyzer each time. Using the vacuum pump system and rinsing out the sample loop at least one or two times before it is placed in line with the carrier gas for injection into the gas chromatograph, usually is sufficient to minimize the possibility of contamination from the previous sample injected by the system.

Another advantage derived from using a vacuum pump is that it permits the system to work with samples which are maintained at less than atmospheric pressure, as well as those at greater than atmospheric pressure. With proper selection of the size of the enclosure and the conduit used to connect the various elements of the system, the sampling efficiency can be maintained at a high level so that the amount of sample wasted is minimized.

The system is designed so that its control is determined solely by the position of the valves. This feature enables the system to be easily adapted to the automatic control system provided herein, so that an entire series of samples can be individually injected into the chromatograph and analyzed in a sequential fashion.

A better understanding of the invention and its advantages can be seen in the following description of the figures and preferred embodiment.

DETAILED DESCRIPTION OF THE DRAWINGS AND PREFERRED EMBODIMENT

FIGS. 2–4 are the same as FIG. 1 with the valves shown in their positions for Steps 2, 3 and 4, respectively.

THE SAMPLE INJECTION SYSTEM

Figure 1:
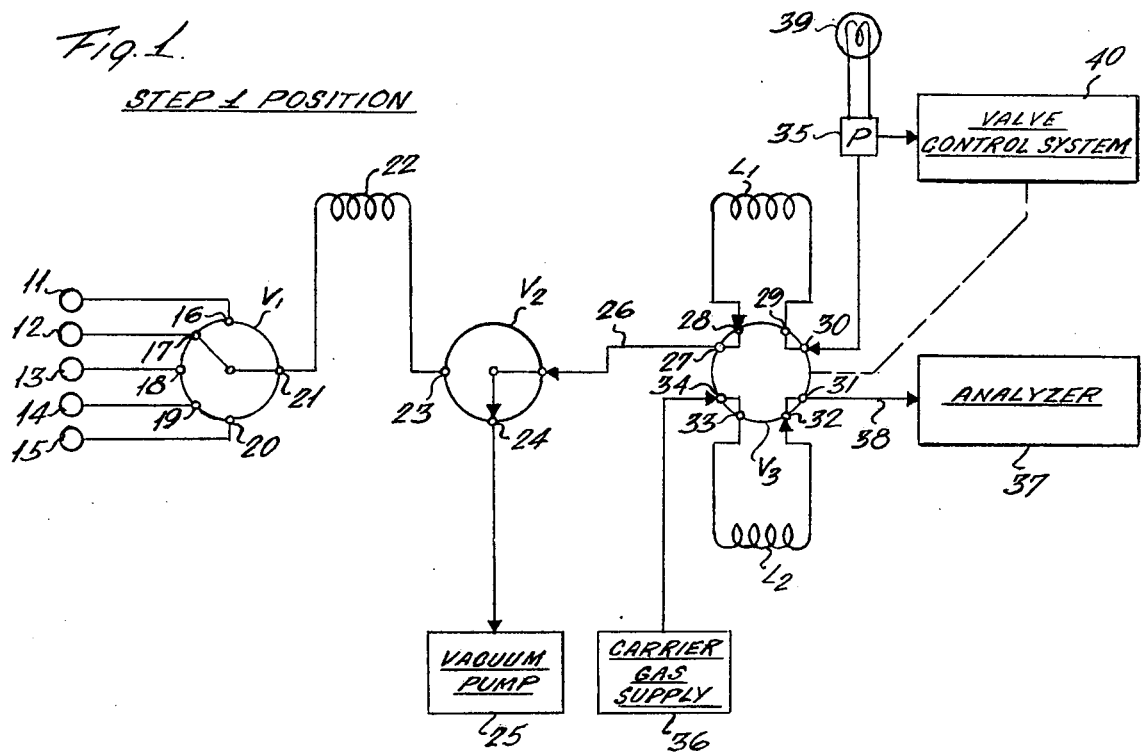
FIG. 1 illustrates a schematic drawing of the vacuum loop sample injection system with the valves in position for Step 1.

The vacuum loop gas injection system is designed so that it can be mounted within an oven such as the oven containing the chromatograph or other analyzer. However, the oven and controls for maintaining the proper temperature therein are not illustrated in the drawing, since they are not part of the invention and the illustration thereof is not necessary for one skilled in the art to practice this invention.

The injection system has three selector valves, V1, V2, and V3 which determine the manner in which the elements of the injection system are connected. These selector valves, with their respective actuator systems, can be any of the many conventional valves currently available for use with gas chromatographs and other similar analyzer systems, or a rotary valve similar to that shown in U.S. Pat. No. 3,223,123 issued to E. T. Young.

Valve V1 is connected so that it can receive samples from a selected number of containers. As is shown in FIG. 1, five sample containers 11, 12, 13, 14 and 15, are connected to parts 16, 17, 18, 19 and 20 on valve V1 through their respective conduit lines. While only five sample containers are shown connected to valve V1, it can be appreciated that the capacity of the injection system can be increased by selection of a valve with a greater capacity. Connected to port 21 of valve V1 is a restriction 22 which acts to slow flow rate of the sample material entering the injection system as well as to smooth out the flow. Preferably, restrictor 22 can be made from a length of small diameter capillary tubes with an inside diameter small enough so that several seconds are necessary for the sample enclosure or loop in the injection system to be filled.

Valve V2 acts as a control valve and has two positions in which either port 23, which is connected to restrictor 22, of port 24, which connects to vacuum pump 25, is connected to port 27 of valve V3 through conduit 26.

Valve V3 also is a two position valve and has eight ports which are interconnected in a manner which will be described below. Two sample loops, L1 and L2, serve as sample enclosures and are connected to valve V3 through ports 28 and 29, and 32 and 33, respectively. While one sample loop would be adequate, more efficient operation is permitted when two loops are used. It should be noted that other alternatives to using sample loops are possible, such as a small passageway within valve V3. Pressure sensor system 35 is connected to port 30 and carrier gas supply 36 is connected to port 34. An analyzer of gas chromatograph 37, which receives the sample volume, is connected to port 31 of valve V3 through injection line 38.

Figure 2:
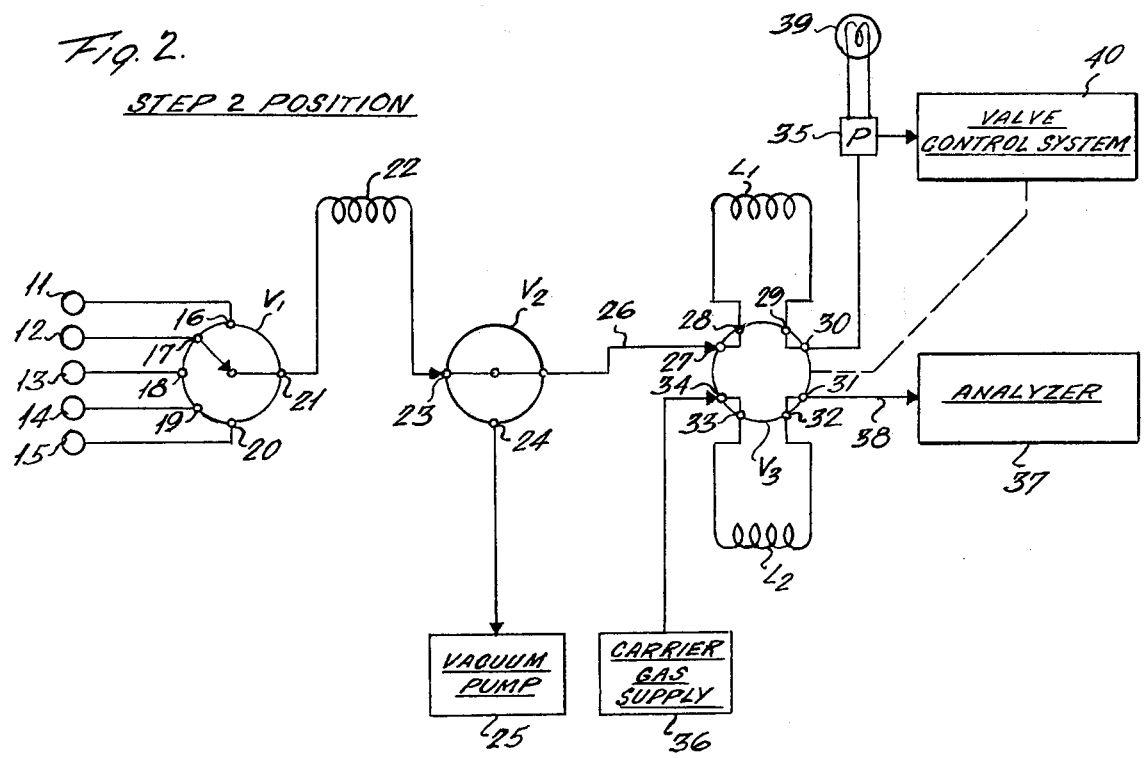

Valve V3 has a first position, which is illustrated in FIGS. 1 and 2, wherein loop L1 is in series with conduit 26 and pressure sensor system 35, and loop L2 is in series with carrier gas supply 36 and injection line 38 leading to analyzer 37. The second position of valve V3 has loop L1 connected in series with carrier gas supply 36 and analyzer 37 and loop L2 connected in series with conduit 26 and pressure sensor 35.

Included within pressure sensor system 35 can be a system for producing a signal which indicates that the pressure sensor has determined that the pressure within a loop has reached a predetermined amount. This signal can be in the form of a light 39 or can be a signal sent to a valve control system for automatically changing the position of valve V3. A more detailed explanation of the operation of these systems will be provided below.

When operating the vacuum loop sample injection system, a desired number of sample containers can be connected to the ports of valve V1. Valve V1 is then set to connect one of the valve ports associated with a particular sample to the exit port 21, such as port 17 which is illustrated in FIG. 1. Valve V2 is set so that vaccum pump 25 is connected to conduit 26. When valve V3 is in the position indicated in FIG. 1, loop L1 will be connected to vacuum pump 25 through valve V2 and also to pressure sensor system 35. At the same time loop L2 is connected in series with carrier gas supply 36 and analyzer 37. What is taking place at this time, is that any sample material that is in loop L2 is being injected into analyzer 37 by the flow of carrier gas from carrier gas supply 36. Also, at the same time, a vacuum is being created within loop L1. The injection system is now at its Step 1 position, as is shown in FIG. 1.

In the Step 2 position, the position of valve V2 is changed so that loop L1 is connected to a sample source, such as container 12, through valves V1 and V2 and restrictor 22. However, the position of valve V3 remains unchanged and carrier gas is still flowing through loop L2. In Step 2, a vacuum is present within loop L1 which acts to pull sample material from container 12 eventually into loop L1. Step 2 continues until the pressure within loop L1 rises to the predetermined amount set on pressure sensor system 35.

Because of restrictor 22, the time to reach this pressure will be several seconds. Once pressure sensor system 35 indicates that the predetermined pressure has been reached, valve V3 then changes into its second position as is illustrated in FIG. 3. The change of valve V3's position can be accomplished manually by having an operator switch the valve position when light 39 lights up or can be done automatically by having a signal sent to a valve control system 40 from pressure sensor system 35.

For purposes of rinsing the injection system out so that contaminants are removed before the sample is analyzed, Step 3 can be delayed so that Step 1 and Step 2 can again be repeated, as often as is deemed necessary. In this manner, the sample is drawn back out of a loop by vacuum pump 25 and new amounts of sample drawn back into the loop. After repeating this sequence of Step 1 and Step 2 a few times, Step 3 can then be initiated.

With the injection system in the Step 3 position, loop L1 is now connected to carrier gas supply 36 and analyzer 37 so that the carrier gas forces the sample collected within loop L1 into analyzer 37 to be analyzed.

Also in the Step 3 position, loop L2 is in position to receive the next sample to be analyzed, in a similar manner as described above for loop L1. Vacuum pump 25 is connected to loop L2 through valve V2, as illustrated in FIG. 4 for the Step 4 position. Valve V1 is also switched to connect the next sample, sample 13 at port 18, to restrictor 22 for later connection to loop L2.

The rinse cycle for loop L2 can now begin by switching the positions of valve V2 so that loop L2 is filled and evacuated a few times as discussed above for loop L1. After an appropriate number of rinses, the position of valve V3 can be reversed back to the position shown in FIGS. 1 and 2 so that the sample collected in loop L2 is against injected into analyzer 37 and loop L1 can be rinsed and filled with the next sample, sample 14.

The pressure sensor system 35 can include a pressure transducer interconnected with a voltage divider circuit so that when the pressure in the loop reaches the predetermined level, the transducer and the voltage divider circuit reach a certain voltage or condition which causes light bulb 39 to light up. The valve control system can be any electrical system which would cause valve V3 to change positions once a certain voltage or condition was reached by the pressure sensor system 35. Systems which perform these functions are readily available to those skilled in the art.

While this sample injection system is primarily designed for laboratory use, it can be equally applicable to process control. Instead of using valve V1, restrictor 22 may be directly connected to a stream in some process. Another alternative would be to circulate several streams through their own sample container in which a sample can be isolated at will and tested as illustrated above.

THE AUTOMATIC CONTROL SYSTEM

An electronic control system for automatically controlling the operation of the sample injection system in the preferred sequence discussed above is also provided herein. When using this control system the operator is able to connect a predetermined number of samples to the selector valve V1 and push a button to initiate the sequential operation of valves V1, V2, and V3 so that the sample loop, L1 or L2, is rinsed out a predetermined number of times by the particular sample, and then the sample is injected into the chromatograph or other analyzer device. At the time of the injection, the other sample loop is placed in position to be rinsed out the predetermined number of times before again returning to the position for injection of the sample therein into the chromatograph. After the particular sample has been injected into the chromatograph a predetermined number of times, the sampling system automatically switches to inject the next sample. When the last sample connected to valve V1 has been injected the predetermined number of times, the system automatically shuts itself off.

Before the operation of the control system is explained in detail, a few preliminary remarks will be made with respect to its components. A starting switch 50 is provided to initiate the sequential operation. A terminal 51, with a green light 52 connected thereto, is provided for connection to the particular gas analyzer or chromatograph 37 into which the sample is to be injected, for the purpose of providing a signal indicating that the analyzer 37 is in a condition for receiving the sample. Therefore, when green light 52 is lit, an indication provided that the analyzer 37 is ready for testing and a "high" condition is present on the second input to AND gate 78. Terminal 53 is provided for receiving the voltage from pressure sensor system 35, which is related to the pressure inside loop L1 or L2. The output voltage produced by pressure sensor system 35 is compared to a voltage received at terminal 54 from reference voltage source 55, which is preset to provide the appropriate reference voltage related to the desired pressure. Amplifier 56 then produces an output pulse or "high" condition when the voltage difference between these two voltages indicates that the pressure in sample loop L1 and L2 has begun to rise above the predetermined level, which also lights red light 57.

A normally closed switch 58 is provided at terminal 59 to provide a hold function. When switch 58 is opened, the condition on the third input terminal of AND gate 86 becomes a "Low", which acts to prevent the actual injection of the sample into the gas analyzer in the event that the operator should desire to continue the sequential operation of the injection system without injecting a sample. Terminal 60 provides a connection for other instruments to record when the sample has been injected into the analyzer if so desired. A switch 61 is provided to enable the operator to manually advance the position of valve V1 to select the sample to be injected.

An automatic shut-off function for the control system is provided by having a valve position indicator 62 interfaced with valve V1, and a readout 63 which indicates the particular position that valve V1 is in, thereby indicating the number of the sample that is connected to valve V1 at any particular time. Valve position indicator 62 designed to provide an output voltage which is related to the particular position of valve V1. Valve position indicator 64 is similar to that provided in indicator 62 and enables a position to be preselected which is related to the desired final position for valve V1. A voltage comparator circuit 65 receives the outputs from switch position indicators 62 and 64 and produces a pulse or "high" condition when the output of indicator 62 reaches that provided by indicator 64. At this time white light 66 lights up to provide a visual indication that the injecting sequence has terminated. As will be described below, this pulse also acts to shut-off and reset the entire control system.

The conditions of the control system immediately before initiation of the sequential operation will now be described. At the termination of the previous sequential operation, the reset terminal of flip-flop 68 will have received a pulse from voltage comparator 65 of the automatic shut-off system, thereby causing the Q output to have a "low" condition. The $\overline{Q}$ output of flip-flop 68 will have a "high" condition which is received by OR gates 69, 70, 71, and 72 to place a "high" condition on input terminal three of AND gate 78 and to hold counters 73 and 74 and flip-flop 75 all in the reset position. The "high" supplied to OR gate 71 acts to place a "high" on the first input terminal of AND gate 76 through flip-flop 77. The positions of valves V1, V2, and V3 at the beginning of a test would be similar to that shown in FIG. 1, except valve V1 would be positioned so that upon its first actuation, sample 11 would be connected to the inlet port of valve V1. As discussed above, one of the sample loops, loop L1 for instance, is being evacuated by vacuum pump 25.

To initiate the sequential operation, starting switch 50 is pressed, which provides a pulse or a "high" on the set terminal of flip-flop 68. The "high" produced on the Q output of flip-flop 68 causes a "high" to be produced on the output of AND gate 78, since all input terminals now have a "high" condition, assuming a high condition on the second input terminal since the chromatograph is ready to receive a sample and on the third input terminal because of the aforementioned procedure of the automatic shut off of the preceeding sequential operation. At the same time the starting pulse is produced, the $\overline{Q}$ output of flip-flop 68 becomes a zero or a "low", and releases OR gates, 69, 70, 71 and 72 so that flip-flops 75 and 77 can operate.

The pulse produced by AND gate 78 is received by the set terminal of flip-flop 75, which produces another pulse on the Q output terminal so that actuator 79 of valve V2 is activated. This actuation causes the position of valve V2 to change from a connection with vacuum pump 25, as is illustrated in FIG. 1, to a connection with restriction 22 as is illustrated in FIG. 2.

The "high" condition produced on the Q output of flip-flop 75 is received by the clock terminal of counter 73, thereby producing a "high" condition on output 1 of counter 73, which places all inputs to AND gate 76 in the "high" condition. The resulting "high" from AND gate 76 creates another "high" condition on the output of OR gate 81, which in turn produces a "high" on the Q output terminal of flip-flop 82, which acts to activate actuator 83 of valve V1. Time delay circuit 84 controls the length of time actuator 83 is activated so that the position of valve V1 is changed to connect the next sample. The actuating pulse for actuator 83 also is received by counter 74 through OR gate 72, for the purpose of resetting this counter, which controls the number of injections for a particular sample, and by flip-flop 77 for the purpose of producing a zero condition on input terminal one of AND gate 76, to prevent any change in the sample selector valve V1 until the preset number of injections on counter 74 have been performed.

While these electrical operations have been taking place, the sample loop has been connected to the sample supply (sample 11) and the sample is slowly being drawn into the loop. As stated above, this filling of the loop with sample is designed to terminate at the time the pressure within the loop reaches a predetermined level so as to obtain reproducible samples with the same pressure, temperature, and volume. As stated above, a pulse will be produced by amplifier 56 at the time the pressure sensed by pressure sensor system 35 reaches the predetermined value. At that time, red light 57 will provide a visual indication that this condition has occured.

Once the correct pressure is detected in sample loop L1, two events can happen. One is the sample can be evacuated by connecting the loop to vacuum pump 25 to effect a rinsing cycle. The other is the sample can be connected in series with carrier gas supply 36 and analyzer 37 for injection, by changing the valve V3 position, and a moment later the other sample loop is connected to vacuum pump 25, the time delay being determined by time delay element 85.

In the first case, assuming the predetermined number of rinses set on counter 73 have not taken place, input terminal one of AND gate 86 has not been properly conditioned by counter 73 to actuate valve V3 to inject the sample. Therefore, the pulse or "high" condition from amplifier 56 passes through OR gate 69 and time delay element 85 to reset flip-flop 75, changing the position of valve V2 back to being connected to vacuum pump 25, as shown in FIG. 1. The "high" produced on the $\overline{Q}$ output terminal of flip-flop 75 because of the reset action will act to switch valve V2 back to its Step 2 position, wherein it is connected to the source of sample after a time delay determined by time delay element 80. A second pulse will be received by counter 73 when the loop is again connected to the sample source. The time setting on element 80 is selected to be sufficiently long to permit evacuation of the sample loop by vacuum pump 25.

Once the predetermined number of rinse cycles have taken place and have been counted by counter 73, AND gate 86 is properly conditioned so that upon receipt of the next pulse from amplifier 56, valve V3 is actuated to its step 3 position. In This position as illustrated in FIG. 3, the carrier gas from supply 36 can empty the sample in the loop into gas analyzer 37.

At the same time valve V3 is activated, counter 73 is reset for counting the next series of rinse cycles by the output pulse from AND gate 86 which passes through OR gate 70. Counter 74 also receives this output pulse on its clock terminal for the purpose of counting the number of times a particular sample is injected into the gas analyzer 37. At the same time, terminal 60, which can be connected to other recording instruments, receives a signal indicating that the sample has been injected.

Immediately after valve V3 changes its position, the Step 4 position, see FIG. 4, is obtained by virtue of the output pulse from amplifier 56 causing valve V2 to return to its position for connection to vacuum pump 25. Time delay element 85 assures this position is not reached until the circuit elements for actuating valve V3 have had a chance to actuate valve V3 if properly conditioned. In this step, sample loop L2 will be subjected to a predetermined number of rinse cycles, after which AND gate 86 will again be conditioned to permit injection of the sample loop L2 to the gas analyzer. After the particular sample (sample 11) has been injected into the gas analyzer the predetermined number of times set on counter 74, a "high" will be provided at the second input terminal of OR gate 71, which places a "high" on the first input terminal of AND gate 76. The second input terminal of AND gate 76 receives a "high" from the resetting of counter 73 by AND gate 86. AND gate 76 is now conditioned to produce an output pulse for changing the position of valve V1 to the next sample (sample 12) upon receipt of a "high" from counter 73. After valve V1 is actuated again, flip-flop 77 is reset so that AND gate 76 is disabled and will not produce an output pulse until the sample is injected into the analyzer the predetermined number of times.

This sequential operation continues until the last sample which is connected to valve V1 is reached. At this time, valve position indicator 62, produces an output which corresponds to the output from valve position indicator 64 which was set at the beginning of the operation for the number of samples to be analyzed. Voltage comparator circuit 65 determines that the outputs are the same and produces a pulse which resets flip-flop 68, thereby disabling AND gates 76 and 78 and reset counters 73 and 74 and flip-flop 75 for the next sequential operation.

Figure 5:
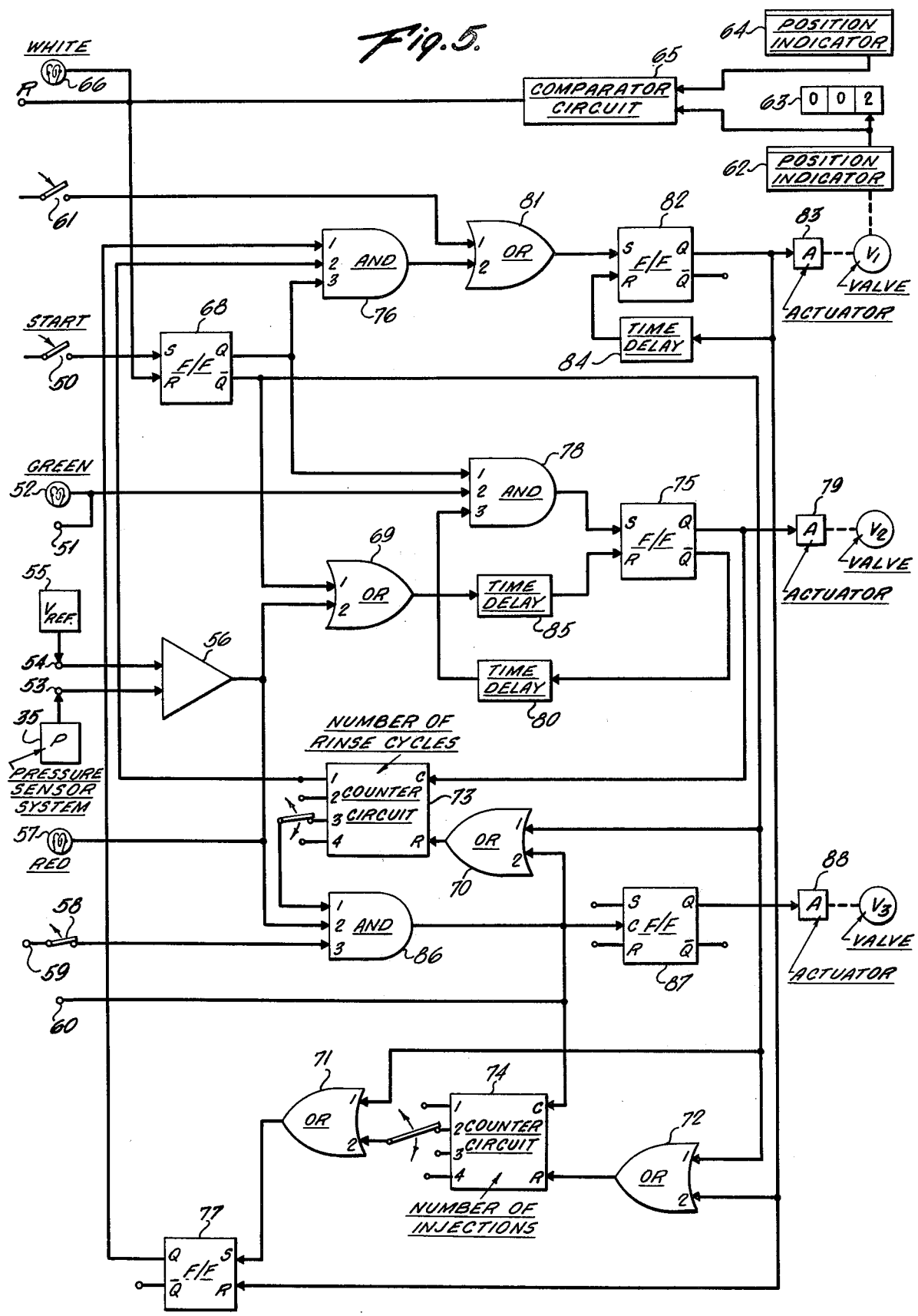
FIG. 5 is a circuit diagram of the automatic control system for the injection system.

While FIG. 5 illustrates on embodiment of an electrical system for accomplishing the sequential operation of this injection system, it should be noted that other circuits and systems can be used to perform the same function, including microprocessors which can be programmed to control the sequential operation in a similar fashion.

While particular embodiments of this invention have been shown and described, it is obvious that changes and modifications can be made without departing from the true spirit and scope of the invention. It is the intention of the appended claims to cover all such changes and modifications.

The invention claimed is:

1. In a vacuum loop sample injection system for injecting a predetermined amount of sample material from at least one sample source into a system for analyzing the sample, said injection system comprising,
   a. a vacuum source;
   b. at least one enclosure means having a predetermined volume;
   c. means for detecting the pressure within the enclosure means and for producing a signal related to the pressure detected;
   d. a source of carrier gas;
   e. first connecting means having a first inlet port connected to the vacuum source, a second inlet port connected to the sample source, and an outlet port, said first connecting means having a first position wherein its first inlet port is in fluid communication with its outlet port, and a second position wherein the second inlet port is in fluid communication with its outlet port; and
   f. second connecting means having a first position wherein the enclosure means is connected to the outlet port of the first connecting means and a second position wherein the enclosure means is placed in series with the carrier gas source and the sample analyzer system so that the carrier gas forces the sample isolated in the enclosure into the analyzing system;
   an improvement for automatically controlling the two connecting means for sequential operation of the injection system, wherein the sequential control system comprises:
   g. means for producing a command signal for initiating the sequential operation;
   h. means, responsive to said command signal, for sequentially moving the first connecting means in a cyclic fashion from the first to the second position and back to the first position for a predetermined number of cycles, each cycle being complete upon the first connecting means reaching its second position, so that the enclosure means is rinsed out with sample material;
   i. means, responsive to the completion of a predetermined number of cycles of the first connecting means, for moving the second connecting means from its first position into its second position, wherein the sample material in the enclosure means is injected into the sample analyzer system by the flow of carrier gas through the enclosure means.

2. The improvement recited in claim 1, wherein the sequentially moving means for the first connecting means comprises:
   a. means, responsive to the command signal, for actuating the first connecting means from its first to its second position;
   b. means, responsive to the pressure detecting means producing a signal indicating a predetermined pressure has been reached in the enclosure means, for actuating the first connecting means from its second to its first position; and
   c. means, responsive to the first connecting means being actuated from its second to its first position, for actuating the first connecting means from its first to its second position a predetermined time interval after the first connecting means is activated from its second to its first position, so that after the command signal is provided, the first connecting means automatically changes positions in a cyclic fashion.

3. The improvement recited in claim 2, wherein the sequentially moving means for the first connecting means further comprises:
   means for counting the number of complete cycles the first connecting means is moved through, and for providing a signal for receipt by the moving means for the second connecting means when a count of a predetermined number has been reached, so that the sample material in the enclosure can be injected into the analyzer system when the predetermined number of cycles has been counted.

4. In a vacuum loop sample injection system for injecting a predetermined amount of sample material from at least one sample source into a system for analyzing the sample, said injection system comprising,
   a. a vacuum source;
   b. at least two enclosure means, each having a predetermined volume;
   c. means for detecting pressure and for producing a signal related to the pressure detected;
   d. a source of carrier gas;
   e. first connecting means having a first inlet port connected to the vacuum source, a second inlet port connected to the sample source, and an outlet port, said first connecting means having a first position wherein its first inlet port is in fluid communication with its outlet port, and a second position wherein the second inlet port is in fluid communication with its outlet port; and
   f. second connecting means having a first position wherein the first enclosure means is connected between the outlet port of the first connecting means and the pressure detecting means, and the second enclosure means is connected between the carrier gas source and the analyzer system, and having a second position wherein the relative positions of the two enclosure means are reversed;
   an improvement for automatically controlling the two connecting means for sequential operation of the injection system, wherein the sequential control system comprises:
   g. means for producing a command signal for initiating the sequential operation;
   h. means, responsive to said command signal, for sequentially moving the first connecting means in a cyclic fashion from the first to the second positions and back to the first position for a predetermined number of cycles, each cycle being complete upon the first connecting means reaching its second position, so that the enclosure means is rinsed out with sample material;
   i. means, responsive to the completion of a predetermined number of cycles of the first connecting means, for moving the second connecting means from its current position into its other position so that the enclosure means containing sample material at the end of the predetermined number of cycles of the first connecting means, is placed in series with the carrier gas supply and the analyzer system for injection of the sample contained therein into the analyzer system, and so that the other enclosure means is connected between the first connecting means outlet and the pressure detection means to be rinsed out and filled with sample material.

5. The improvement recited in claim 4, wherein the sequentially moving means for the first connecting means comprises:
   a. means, responsive to the command signal, for actuating the first connecting means from its first to its second position;
   b. means, responsive to the pressure detecting means producing a signal indicating a predetermined pressure has been reached in the enclosure means, for actuating the first connecting means from its second to its first position; and
   c. means, responsive to the first connecting means being actuated from its second to its first position, for actuating the first connecting means from its first to its second position a predetermined time interval after the first connecting is activated from its second to its first position, so that after the command signal is provided, the first connecting means automatically changes positions in a cyclic fashion.

6. The improvement recited in claim 5, wherein the sequentially moving means for the first connecting means further comprises:
   means for counting the number of complete cycles the first connecting means is moved through and for providing a signal for receipt by the moving means for the second connecting means when a count of a predetermined number has been reached, so that the sample material in the enclosure can be injected into the analyzer system when the predetermined number of cycles has been counted.

7. The improvement recited in claim 6, wherein the sample source includes several samples in their separate sample container or source to be injected individually, and the sample injection system also includes a third connecting means connected to the first connecting means for selecting the sample container or source from which the sample material is to be drawn; and the improvement further comprises means, responsive to the movement of the second connecting means from one position to the other, for advancing the third connecting means to connect the next sample container or source so that the sample material therein can be injected.

8. The improvement recited in claim 7, wherein the advancing means further comprises:
   a. means for counting the number of times a sample from a sample container is injected, and for producing an indicator signal when the sample from a sample container has been injected a predetermined number of times; and
   b. means, responsive to said indicator signal, for actuating the advancing means to move the third connecting means to connect the next sample container.

9. The improvement recited in claim 8, further comprising means for stopping the sequential operation in response to all sample containers having been connected to the third connecting means.

10. A vacuum loop sample injection system as set forth in claim 4 wherein said means for sequentially moving the first connecting means in a cyclic fashion comprises:
    a. a bistable circuit, responsive to a first input signal to produce a first output signal which causes the first connecting means to move from its first position to its second position, and responsive to a second input signal from the pressure detecting means to change state and produce a second output signal for causing said first connecting means to move to its first position;
    b. a time delay circuit, coupled to receive the second output signal from said bistable circuit and delay it for a given period of time; and
    c. an AND gate, having the command signal as one input and the output of said time delay circuit as a second input, responsive to a signal on both of said inputs to produce an output signal, wherein said AND gate is coupled to the bistable circuit so that the output signal of the AND gate becomes the first input signal to said bistable circuit, to cause said bistable circuit to change state from the production of the second output signal to the production of the first output signal, whereby the first connecting means is moved in a cyclic fashion from the first to the second position and back to the first position.

11. The improvement recited in claim 10, further comprising:
    a. counting means, responsive to the first output signal of the bistable circuit, for producing a output signal indicating that the first connecting means has been placed in its second position a predetermined number of times;
    b. second AND gate means, having the output of the counting means as one input and the output of the pressure detecting means as a second input, responsive to a signal on both of said inputs to produce an output signal;
    c. means, responsive to the output signal of the second AND gate means for moving the second connecting means from one position to the other position, so that the enclosure means has been rinsed out with the sample material and contains the proper amount of sample material when it is injected into the analyzer; and
    d. means, responsive to the output signal of the second AND gate means, for resetting the counting means.

12. The improvement recited in claim 11, wherein the sample source includes several samples in their respective sample container or source to be injected into the analyzer by the sample injection system individually, and the sample injection system also includes a third connecting means, having its output connected to the second inlet port of the first connecting means, for selecting the sample container or source from which an amount of sample material is to be drawn for injection, and the improvement further comprises:
    a. second counter means, responsive to the output signal from the second AND gate means, for counting the number of signals received and for producing an output signal when that predetermining number is reached;
    b. means, responsive to the output signal of the second counter means, for actuating the third connecting means so that the next sample container is connected for injection; and c. means, responsive to the third connecting means being actuated, for resetting the second counting means.

13. The improvement recited in claim 12, further comprising means for stopping the sequential operation in response to all sample containers having been connected to the third connecting means.

* * * * *